United States Patent
Fisher et al.

(10) Patent No.: US 10,786,282 B2
(45) Date of Patent: Sep. 29, 2020

(54) ANTI-MICROBIAL IMPLANT

(71) Applicant: DePuy Synthes Products, Inc., Raynham, MA (US)

(72) Inventors: Michael Alan Fisher, Lawrenceville, GA (US); Hassan Serhan, South Easton, MA (US); John Riley Hawkins, Cumberland, RI (US); Michael Andrew Slivka, Taunton, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 16/039,889

(22) Filed: Jul. 19, 2018

(65) Prior Publication Data

US 2018/0317968 A1 Nov. 8, 2018

Related U.S. Application Data

(62) Division of application No. 14/980,560, filed on Dec. 28, 2015, now Pat. No. 10,064,655, which is a (Continued)

(51) Int. Cl.
*A61B 17/70* (2006.01)
*A61M 31/00* (2006.01)
(Continued)

(52) U.S. Cl.
CPC .......... *A61B 17/70* (2013.01); *A61B 17/685* (2013.01); *A61B 17/7001* (2013.01); *A61B 17/7002* (2013.01); *A61B 17/7032* (2013.01); *A61B 17/7035* (2013.01); *A61B 17/7037* (2013.01); *A61B 17/7091* (2013.01); *A61B 17/84* (2013.01); *A61B 17/86* (2013.01); *A61B 17/8605* (2013.01); *A61B 17/8685* (2013.01); (Continued)

(58) Field of Classification Search
CPC . A61B 2017/561; A61B 17/685; A61B 17/70; A61B 17/7001; A61B 17/7002; A61B 17/7032; A61B 17/7035; A61B 17/7037; A61B 17/7041; A61B 17/7091; A61B 17/84; A61B 17/86; A61B 17/8685; A61B 2017/00889; A61M 31/002
See application file for complete search history.

(56) References Cited

U.S. PATENT DOCUMENTS

| 1,152,960 A | 9/1915 | Moloney |
| 3,797,485 A * | 3/1974 | Urquhart .............. A61K 9/0024 604/288.04 |

(Continued)

FOREIGN PATENT DOCUMENTS

| EP | 754064 | 1/1997 |
| EP | 792654 | 10/2001 |

(Continued)

OTHER PUBLICATIONS

Allcock, in *The Encyclopedia of Polymer Science*, vol. 13, pp. 31-41, Wiley Intersciences, John Wiley & Sons, 1988.
(Continued)

*Primary Examiner* — Larry E Waggle, Jr.

(57) ABSTRACT

Non-load-bearing, drug-eluting components, such as a rod cover, that can be added to load bearing spinal implants.

6 Claims, 18 Drawing Sheets

Related U.S. Application Data division of application No. 11/863,547, filed on Sep. 28, 2007, now Pat. No. 9,247,973.

(51) Int. Cl.
| | |
|---|---|
| A61B 17/86 | (2006.01) |
| A61B 17/84 | (2006.01) |
| F16B 37/14 | (2006.01) |
| A61B 17/68 | (2006.01) |
| A61B 17/56 | (2006.01) |
| A61B 17/00 | (2006.01) |

(52) U.S. Cl.
CPC ............ *A61M 31/002* (2013.01); *F16B 37/14* (2013.01); *A61B 2017/00889* (2013.01); *A61B 2017/561* (2013.01)

(56) References Cited

U.S. PATENT DOCUMENTS

| | | | |
|---|---|---|---|
| 3,918,440 | A | 11/1975 | Kraus |
| 4,105,034 | A | 8/1978 | Shalaby |
| 4,130,639 | A | 12/1978 | Shalaby |
| 4,140,678 | A | 2/1979 | Shalaby |
| 4,141,087 | A | 2/1979 | Shalaby |
| 4,205,399 | A | 6/1980 | Shalaby |
| 4,208,511 | A | 6/1980 | Shalaby |
| 4,442,133 | A | 4/1984 | Greco |
| 4,476,590 | A | 10/1984 | Scales |
| 5,098,434 | A | 3/1992 | Serbousek |
| 5,464,929 | A | 11/1995 | Bezwada |
| 5,595,751 | A | 1/1997 | Bezwada |
| 5,597,579 | A | 1/1997 | Bezwada |
| 5,607,687 | A | 3/1997 | Bezwada |
| 5,618,552 | A | 4/1997 | Bezwada |
| 5,620,698 | A | 4/1997 | Bezwada |
| 5,645,850 | A | 7/1997 | Bezwada |
| 5,648,088 | A | 7/1997 | Bezwada |
| 5,667,508 | A | 9/1997 | Errico |
| 5,698,213 | A | 12/1997 | Jamiolkowski |
| 5,700,583 | A | 12/1997 | Jamiolkowski |
| 5,730,130 | A | 3/1998 | Fitzpatrick |
| 5,791,848 | A | 8/1998 | Lanham |
| 5,833,418 | A | 11/1998 | Shoji |
| 5,859,150 | A | 1/1999 | Jamiolkowski |
| 5,866,113 | A | 2/1999 | Hendriks |
| 5,879,117 | A | 3/1999 | Chen |
| 5,895,427 | A | 4/1999 | Kuslich |
| 5,904,383 | A | 5/1999 | van der Wal |
| 5,947,893 | A | 9/1999 | Agrawal |
| 5,988,966 | A | 11/1999 | Chen |
| 6,077,262 | A | 6/2000 | Schlapfer |
| 6,102,914 | A | 8/2000 | Bulstra |
| 6,241,731 | B1 | 6/2001 | Fiz |
| 6,478,797 | B1 | 11/2002 | Paul |
| 6,514,517 | B2 * | 2/2003 | Jamiolkowski ............ A61L 2/16 424/426 |
| 6,575,945 | B2 | 6/2003 | Prosl |
| 6,663,634 | B2 | 12/2003 | Ahrens |
| 6,887,270 | B2 | 5/2005 | Miller |
| 6,921,390 | B2 | 7/2005 | Bucay Couto |
| 6,936,270 | B2 | 8/2005 | Watson |
| 7,063,701 | B2 | 6/2006 | Michelson |
| 7,066,938 | B2 | 6/2006 | Slivka |
| 7,192,445 | B2 | 3/2007 | Ellingsen |
| 7,435,256 | B2 | 10/2008 | Stenzel |
| 7,819,899 | B2 | 10/2010 | Lancial |
| 8,062,340 | B2 | 11/2011 | Berrevoets |
| 2001/0010016 | A1 | 7/2001 | Modak |
| 2002/0029043 | A1 | 3/2002 | Ahrens |
| 2002/0173775 | A1 | 11/2002 | Modak |
| 2002/0183757 | A1 | 12/2002 | Michelson |
| 2002/0193879 | A1 | 12/2002 | Seder |
| 2003/0036761 | A1 | 2/2003 | Smothers |
| 2003/0078661 | A1 | 4/2003 | Houfburg |
| 2003/0100896 | A1 | 5/2003 | Biedermann |
| 2003/0120276 | A1 | 6/2003 | Tallarida |
| 2003/0139811 | A1 | 7/2003 | Watson |
| 2003/0144666 | A1 | 7/2003 | Bagga |
| 2003/0153983 | A1 | 8/2003 | Miller |
| 2004/0138660 | A1 | 7/2004 | Serhan |
| 2004/0170487 | A1 | 9/2004 | Thompson |
| 2004/0249441 | A1 | 12/2004 | Miller |
| 2005/0031665 | A1 | 2/2005 | Watson |
| 2005/0049596 | A1 | 3/2005 | Stewart |
| 2005/0055096 | A1 | 3/2005 | Serhan |
| 2005/0059972 | A1 | 3/2005 | Biscup |
| 2005/0159805 | A1 | 7/2005 | Weber |
| 2005/0171538 | A1 * | 8/2005 | Sgier ............... A61B 17/7032 606/269 |
| 2005/0171543 | A1 * | 8/2005 | Timm ............... A61B 17/7007 606/257 |
| 2005/0192576 | A1 | 9/2005 | Michelson |
| 2005/0197634 | A1 | 9/2005 | Raad |
| 2005/0215998 | A1 | 9/2005 | Donath |
| 2005/0216010 | A1 | 9/2005 | Michelson |
| 2005/0251139 | A1 | 11/2005 | Roh |
| 2005/0273101 | A1 | 12/2005 | Schumacher |
| 2005/0273104 | A1 | 12/2005 | Oepen |
| 2006/0041261 | A1 | 2/2006 | Osypka |
| 2006/0058791 | A1 | 3/2006 | Broman |
| 2006/0084989 | A1 | 4/2006 | Dickinson |
| 2006/0085791 | A1 | 4/2006 | Day |
| 2006/0089646 | A1 | 4/2006 | Bonutti |
| 2006/0093646 | A1 | 5/2006 | Cima |
| 2006/0149241 | A1 | 7/2006 | Richelsoph |
| 2006/0173456 | A1 | 8/2006 | Hawks |
| 2006/0206207 | A1 | 9/2006 | Dryer |
| 2006/0241601 | A1 | 10/2006 | Trautwein |
| 2006/0276788 | A1 | 12/2006 | Berry |
| 2007/0073300 | A1 | 3/2007 | Attawia |
| 2007/0083265 | A1 | 4/2007 | Malone |
| 2007/0173819 | A1 | 7/2007 | Sandlin |
| 2007/0224243 | A1 | 9/2007 | Bayston |
| 2008/0086214 | A1 | 4/2008 | Hardin |
| 2008/0147127 | A1 | 6/2008 | Tipirneni |
| 2008/0183152 | A1 | 7/2008 | Raad |
| 2008/0221624 | A1 | 9/2008 | Gooch |
| 2008/0255622 | A1 | 10/2008 | Mickiewicz |
| 2009/0005820 | A1 | 1/2009 | Bloebaum |
| 2011/0295253 | A1 | 12/2011 | Bonutti |

FOREIGN PATENT DOCUMENTS

| | | |
|---|---|---|
| WO | WO 199714447 | 4/1997 |
| WO | WO 1998003209 | 1/1998 |
| WO | WO 2002036175 | 5/2002 |
| WO | WO 2007092869 | 8/2007 |

OTHER PUBLICATIONS

Cohn Polymer Preprints (ACS Division of Polymer Chemistry), vol. 30(1), p. 498, 1989.

Cohn and Younes Journal of Biomaterials Research, vol. 22, pp. 993-1009, 1988.

Heller in *Handbook of Biodegradable Polymers*, edited by Domb, et al, Hardwood Academic Press, pp. 99-118 (1997).

Kemnitzer and Kohn, in the *Handbook of Biodegradable Polymers*, edited by Domb, et. al., Hardwood Academic Press, pp. 251-272 (1997).

Vandorpe, et al in the *Handbook of Biodegradable Polymers*, edited by Domb, et al, Hardwood Academic Press, pp. 161-182 (1997).

Buchholz, "Management of Deep Infection of Total Hip Replacement", J Bone Joint Surg Br., 1981, pp. 342-53, vol. 63.

Trebse, "Treatment of Infected Retained Implants", J Bone Joint Surgery Br., 2005, pp. 249-56, vol. 87(2).

Bullock, "A Double-blind Placebo-controlled Trial of Perioperative Prophylactic Antibiotics for Elective Neurosurgery", J Neurosurgery, 1988, pp. 687-91, vol. 69.

Djindjion, " Antibiotic Prophylaxis During Prolonged Clean Neurosurgery", J Neurosurgery, 1990, pp. 383-386, vol. 73.

(56) References Cited

OTHER PUBLICATIONS

Geraghty, "Antibiotic Prophylaxis in Neurosurgery—A Randomized Controlled-trial", J Neurosurgery, 1984, pp. 724-726, vol. 60.
Fang, "Risk Factors for Infection After Spinal Surgery", Spine, 2005, pp. 1460-1465, vol. 30(12).
Blam, "Risk Factors for Surgical Site Infection in the Patient with Spinal Injury", Spine, 2003, pp. 1475-80, vol. 28(13). (Abstract only).
Clark, "Late-developing Infection in Instrumental Idiopathic Scoliosis", Spine, 1999, pp. 1909-12, vol. 24(18) (Abstract only).
Richards, "Delayed Infections After Posterior TSRH Spinal Instrumentation for Idiopathic Scoliosis: Revisited", Spine, 2001, pp. 1990-1996, vol. 26(18). (Abstract only).
Richards, "Delayed Infections Following Posterior-spinal Instrumentation for Idiopathic Scoliosis", J Bone Joint Surgery, 1995, pp. 524-529, vol. 77. (Abstract only).
Darouchie, "Treatment of Infections Associated with Surgical Implants", N Engl J Med, 2004, pp. 1422-1429, vol. 350(14).

\* cited by examiner

ANTI-MICROBIAL IMPLANT

CONTINUING DATA

This application is a division of and claims priority from co-pending application U.S. Ser. No. 14/980,560, filed Dec. 28, 2015 entitled "Anti-Microbial Implant" (Fisher) and from U.S. Ser. No. 11/863,547, filed Sep. 28, 2007, entitled "Anti-Microbial Implant" (Fisher), the specifications of which are incorporated by reference in their entireties.

BACKGROUND OF THE INVENTION

Implant-associated infections are deep wound infections that occur at or near the site of an implanted device and frequently require a second surgery to remove the implant. (refs. 1,2) Retrospective studies of spinal surgery procedures involving implants report infection rates of 1.7% to 17%. (refs. 3-6) The highest incidences of implant-associated infections have been reported for spinal trauma procedures (9-17%) (ref. 7) and scoliosis/deformity procedures (1.7-11%) (refs. 8-11). The average cost of an orthopedic implant-associated infection is $15,000 (ref. 12), and the cost for scoliosis instrumentation is reported to be $65,000. (ref 13) The cost of treating individual infections has been estimated as roughly $22,170 per occurrence. The cost of implant infections in spine surgery divided by the total number of spine patients is estimated to be about $2,400/patient. Third-party payers and patients assume some of these costs, but hospitals and physicians are asked to absorb the remainder.

This cost data suggests the need for a product that minimizes infection rates or mitigates the consequences of infections in spine surgery and that costs less than $2,400 per surgery. Such a product would be valuable to patients, surgeons, hospitals, and medical insurers while also having equitable benefits for healthcare economics.

There are no commercially available spinal products specifically designed to treat or manage implant-associated infections in spine surgery. Although technology exists in the areas of anti-infective coatings and drug-eluting materials, no technology has been developed that describes spinal device components with anti-infective properties.

Some conventional technologies for preventing or managing infection associated with implants are provided in the following patent documents: EP754064, entitled "Polymer Coating for Orthopedic Devices"; EP792654, entitled "Antimicrobial Pin Sleeve"; US2002/0029043, entitled "Silver Bone Screw" and assigned to Synthes; US2003/0036761, entitled "Pharmacological Pin Sleeve" and assigned to Smith & Nephew Richards; US2005/0031665, entitled "Orthopedic Screw Delivery System"; US2005/0059972, entitled "Screw Assembly with Antimicrobial Properties"; US2006/0093646, entitled "Drug Eluting Orthopedic Hip Implant"; U.S. Pat. No. 4,442,133, entitled "Preoperative Anti-Biotic Graft Coating"; U.S. Pat. No. 4,476,590, entitled "Silver Antimicrobial surgical implants"; U.S. Pat. No. 5,098,434, entitled "Porous Coated Bone Screw"; U.S. Pat. No. 6,514,517, entitled "Prevention of Biofilms" and assigned to Ethicon; U.S. Pat. No. 6,575,945, entitled "Prevention of Biofilms"; U.S. Pat. No. 6,663,634, entitled "Bone Screw" and assigned to Synthes; U.S. Pat. No. 6,921,390, entitled "Antibiotic Sleeve" and assigned to BostonScientific; U.S. Pat. No. 6,936,270, entitled "Orthopedic Screw Drug Delivery System and assigned to Control Delivery Systems, Inc; U.S. Pat. No.7,066,938, entitled "Snap-On Rod Connector" and assigned to DePuy Spine; and WO2002036175, entitled "Orthopedic Screw Drug Delivery System" and assigned to Control Delivery Systems.

WO1998003209, entitled "Screw Cap contoured" describes a non-load bearing screw cap that facilitates revision of the implanted screw.

SUMMARY OF THE INVENTION

The present invention relates to non-load-bearing, drug-eluting components that can be attached to load-bearing spinal implants. Preferably, these components elute anti-microbial compounds into the regions in and around the load bearing spinal implants.

The drug-eluting device of the present invention is designed to be a non-load-bearing component (such as a screw cap or rod cover) that fits onto or over conventional structural spinal implants. The geometry of the drug-eluting device of the present invention may be designed to uniquely conform to the spinal products of a single manufacturer, or the device could be made to work with a wide variety of product geometries.

Some embodiments of the present invention take the form of an implantable "screw-spacer" between screw heads or of a "rod-spacer" similar in form to a transverse cross connector. In these embodiments, the device acts as a non-load bearing cover or strut of material associated with the implant construct. Thus, the invention can be load-bearing or non-load bearing.

Drug-eluting devices provide benefits over systemic drug-delivery because the amount of the dose, the location of the dose and the duration of the dose can be controlled by device design. For drug-eluting devices, local drug dose and duration are controlled by the carrier material's resorption rate and geometric surface area, and/or the drug's diffusion in tissue. Providing an anti-infective functionality as a component of a spine instrumentation system may also allow for simpler product regulation as a combination device. It may also allow the drug-eluting functionality to be manufactured, packaged, stored, and distributed separately from the associated structural rods and screws. Lastly, the device could be used for the prophylactic treatment of post-surgical infections.

In one method of using the present invention, the drug-eluting device of the present invention is attached in the operative setting to an implanted orthopedic or spinal product for the purpose of preventing the inoculation or growth of microbes on or near the implant.

In another method of using the present invention, the drug-eluting device of the present invention treats an infected implant by concentrating anti-microbial pharmaceutical compounds in the region of the biofilm on the implant surface. Thus, antibiotics leach from the invention and concentrate on, around, or near the biofilm-coated implant, wherein little or no antibiotic leaches away from the implant. The directionality of this device enables the use of very high concentrations of antibiotics or very aggressive antibiotic molecules (e.g., vancomycin instead of gentamicin).

Also, drug-eluting devices of the present invention can be further designed to elute drugs over a prolonged period of time to increase their local efficacy.

The drug-eluting implant of the present invention may be either a surface-eroding device or a bulk eroding biodegradable device containing an adequate anti-bacterial pharmaceutical, such as gentamicin or tobramycin. As the drug-eluting implant erodes or degrades, the anti-bacterial pharmaceutical contained in the device leaches or diffuses into surrounding tissues for a local anti-microbial action. Because the drug is not delivered systemically, many drug-related side effects can be minimized and the "minimum effective concentration" (MEC) of the drug can be maintained at the site of need for a prolonged period of time.

Maintaining a high local concentration of an anti-bacterial drug should greatly diminish acute wound infections (99% of all hospital infections) and also decrease implant-associated infections (1-2% of all infections, but devastating when present).

Embodying the invention in a separate device that physically attaches to the structural spinal implant avoids many of the problems associated with drug-coated devices (inventory, sterilization, packaging, handling, shelf-life, altered biomechanics, etc.) and streamlines the regulatory process.

Therefore, in accordance with the present invention, there is provided a spinal screw assembly, comprising:
 a) a load bearing spinal component,
 b) a non-load bearing spinal component comprising a pharmaceutical compound,
wherein the non-load bearing spinal component is attached to the load bearing spinal component.

Therefore, in accordance with the present invention, there is provided a method of making a spinal screw assembly, comprising the steps of:
 a) providing a load bearing spinal component,
 b) providing a non-load bearing spinal component comprising a pharmaceutical compound,
 b) attaching the non-load bearing spinal component to the load bearing spinal component.

DETAILED DESCRIPTION OF THE INVENTION

Figure 1A:
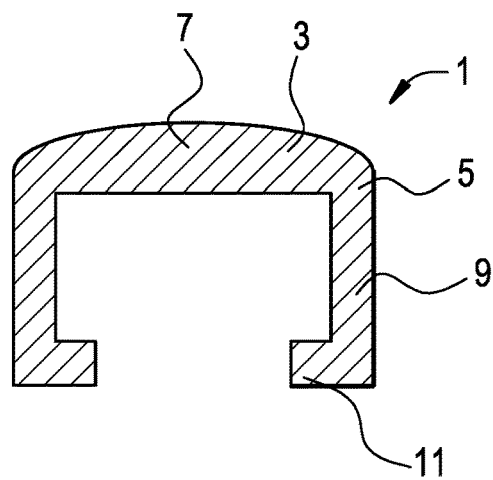
FIG. 1a discloses a cross section of a bone screw cap of the present invention having a flange.
Figure 1B:
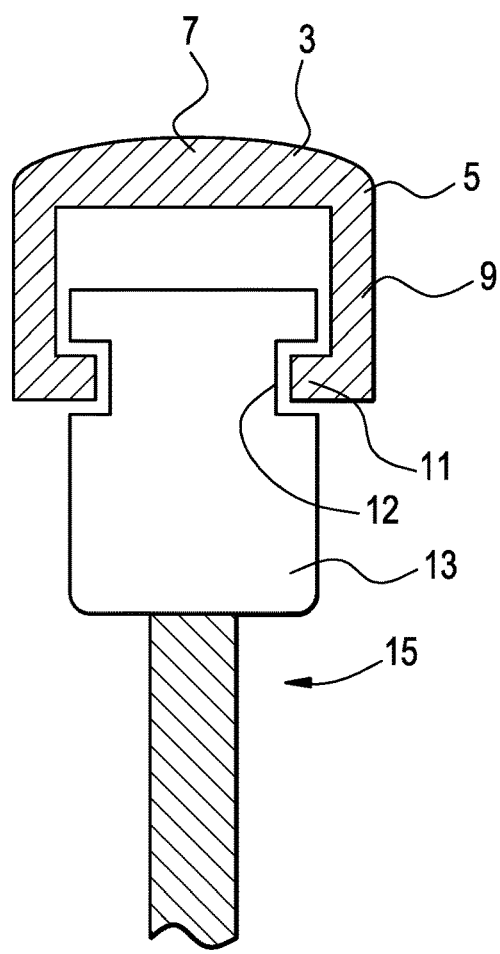
FIG. 1b discloses a cross section of the bone screw cap of FIG. 1a fitted upon a bone screw head.

Now referring to FIGS. 1a and 1b, there is provided a bone screw cap 1 loaded with a pharmaceutical compound, and comprising:
 a) a cover 3 having a perimeter 5 and a center 7,
 b) a shank 9 extending downwardly from the perimeter of the cover,
 c) a flange 11 extending inwardly from the shank and adapted to engage a recess in a side of the bone screw,
wherein the shank fits substantially closely to an outer contour 12 of a head 13 of a bone screw 15.

Figure 2:
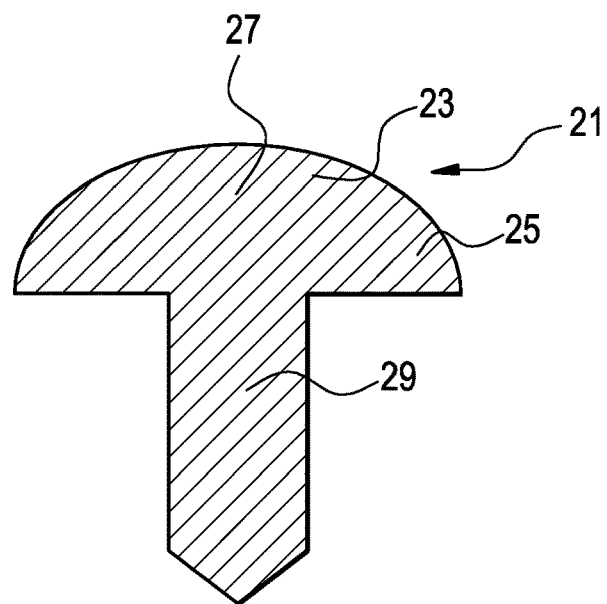
FIG. 2 discloses a cross section of a bone screw cap of the present invention having a central shank.
Figure 3:
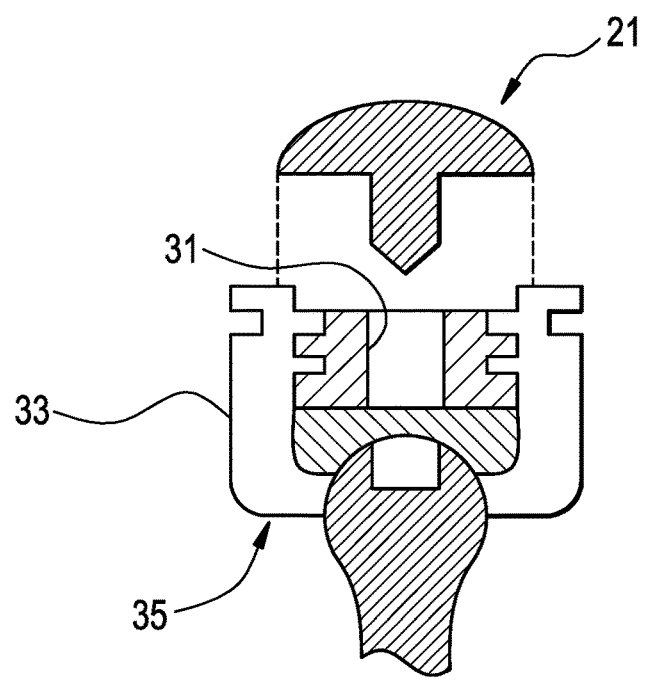
FIG. 3 discloses a cross section of the bone screw cap of FIG. 2 fitted upon a bone screw head.

Now referring to FIGS. 2 and 3, there is provided a bone screw cap 21 loaded with a pharmaceutical compound, and comprising:
 a) a cover 23 having a perimeter 25 and a center 27,
 b) a shank 29 extending downwardly from the center of the cover,
wherein the shank fits substantially closely to an inner contour 31 of a head 33 of a bone screw 35.

The bone screw cap of the present invention is preferably adapted to fit over the conventional polyaxial pedicle screw that is used in spinal surgery. In many embodiments, the pedicle screw has a substantially cylindrical upper portion (or head) and the cap is adapted to fit over this cylindrical portion. In some embodiments, the cap is a snap-on type having features that mate with corresponding mating features provided on the cylindrical upper portion of the pedicle screw. Pharmaceuticals eluted from the bone screw cap can provide their highest concentration in and around the bone screw, which is the site of the most complicated geometry of the conventional spinal implant, and at which it is hypothesized that latent microbes gain a foothold and proliferate. The dose of pharmaceutical delivered by the screw cap as well as its duration can be increased by increasing the thickness of the cap.

Figure 4:
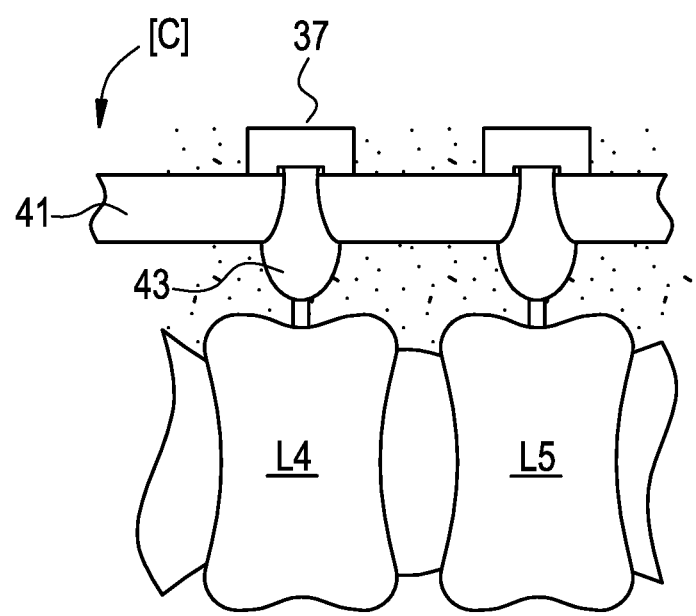
FIG. 4 discloses a drug concentration around a spinal assembly having a bone screw cap of the present invention.

Now referring to FIG. 4, there is provided a side view of a screw cap 37 of the present invention attached to a spinal implant system that is implanted in a spine, wherein the spinal implant system comprises rods 41 and screws 43. There is a high concentration [C] of the pharmaceutical present in the regions directly adjacent the screw cap, and this concentration lessens with increasing distance from the screw cap. This embodiment also provides a relatively severe local concentration gradient around the screw cap. The severity of the gradient is likely due to the relatively small size of the screw cap relative to the overall implant system. The elution profile of the pharmaceutical will likely change as the screw cap degrades or dissolves, thereby making the concentration a function of location, cap geometry, implant system geometry, and time.

In some embodiments, the means for connecting the cap to the bone screw comprises an adhesive or a curing composition.

Figure 5:
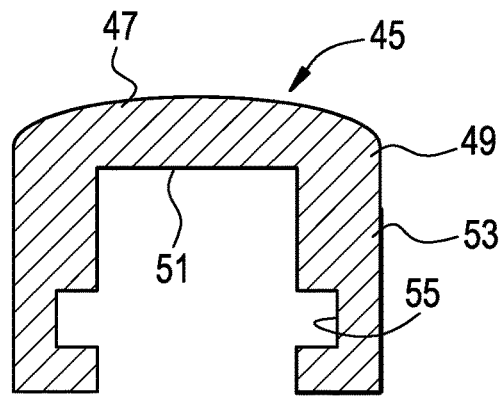
FIG. 5 discloses a cross section of a bone screw cap of the present invention having a recess.
Figure 6:
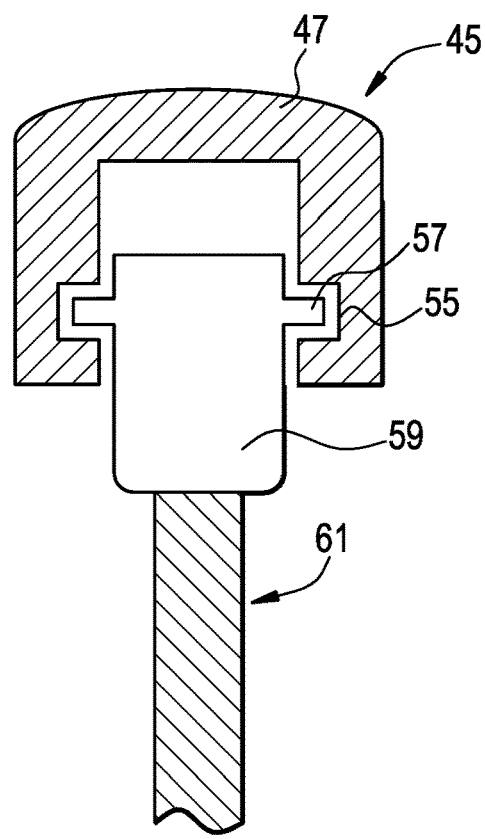
FIG. 6 discloses a cross section of the bone screw cap of FIG. 5 fitted upon a bone screw head.

In some embodiments, and now referring to FIGS. 5-6, there is provided a press-fit bone screw cap 45 having:
 a) a cover 47 having a perimeter 49 and a center 51,
 b) a shank 53 extending downwardly from the perimeter of the cover, and
 c) a recess 55 extending into the shank and adapted to engage a flange 57 extending outwardly from a head 59 of a bone screw 61.

This cap attaches to external screw head features, such as a flange extending radially from the cylindrical portion of the conventional polyaxial pedicle screw.

Figure 7:
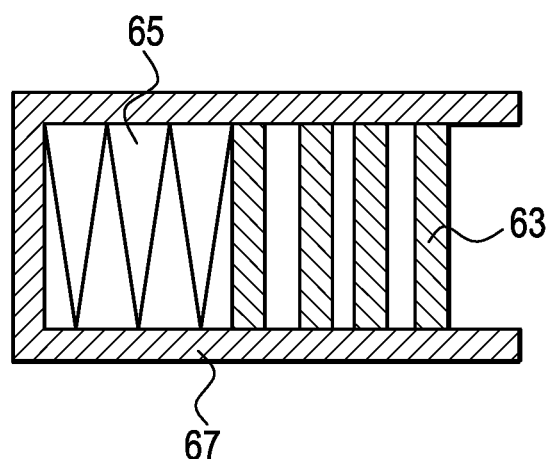
FIG. 7 discloses a cross section of a plurality of bone screw caps housed in a spring loaded container.

Now referring to FIG. 7, in some embodiments, the press-fit screw caps 63 of the present invention can be stored in a stack-wise fashion in a spring-loaded 65 dispenser 67 and used on an as-needed basis.

Figure 8:
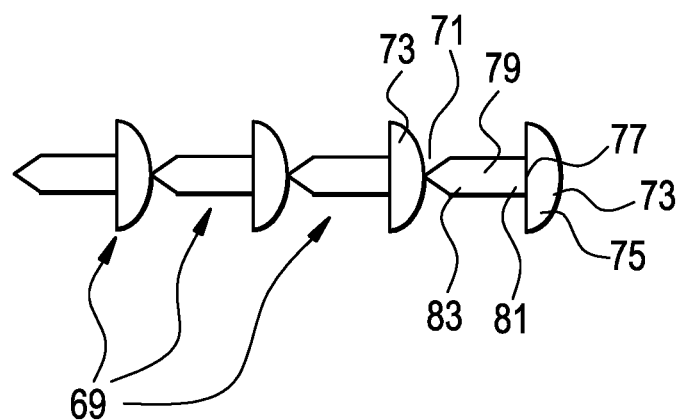
FIG. 8 discloses a plurality of bone screw caps of the present invention joined together.

Now referring to FIG. 8, in some embodiments, a plurality of connected press-fit screw caps 69 of the present invention can be provided in a tip-to-toe fashion. Individual caps are separated from the assembly by breaking them at a fracture point 71 present between the tip of one cap and the toe of the adjacent cap, and used on an as-needed basis. The design of this embodiment lends itself to manufacture by an extrusion process.

Still referring to FIG. 8, there is provided a plurality of connected bone screw caps 69 loaded with a pharmaceutical compound, wherein each cap comprises a:
 a) a cover 73 having a perimeter 75 and a center 77,
 b) a shank 79 having a first end 81 connected to the center of the cover and a second end 83,
wherein the shank fits substantially closely to an inner contour of a head of a bone screw, and wherein the second end 83 of a first screw cap is connected to the cover 73 of a second screw cap at a fracture point 71.

Figure 9:
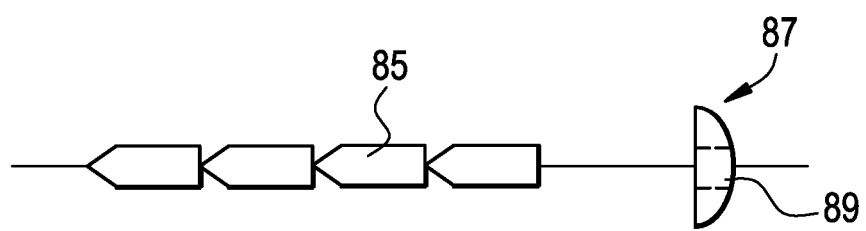
FIG. 9 discloses an exploded version of a plurality of bone screw cap posts joined together with a cover.
Figure 10:
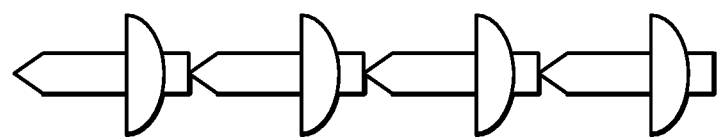
FIG. 10 discloses an integral version of a plurality of bone screw caps joined together.

However, now referring to FIG. 9, other embodiments of the present invention use modular screw caps, wherein the shank 85 and a cover 87 having a central throughhole 89 are manufactured separately and then assembled by overmolding, by fitting the shank through the throughhole of the cover. In these embodiments, the shanks can be provided as a plurality of shanks wherein the first end of a first shank is connected to the second end of a second shank by a fracture point. FIG. 10 shows the assembled modular embodiment.

Figure 11:
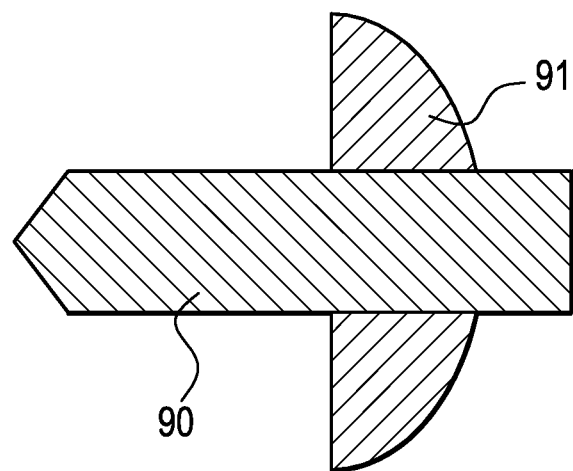
FIG. 11 discloses a cross section of bone screw cap having a cover of a first material and a post of a second material.

In the embodiments of FIG. 11, the shank 90 (which primarily has an attachment function) is generally made of a strong and rigid first material that is slow to resorb. Preferably, the shank carries a high concentration of the pharmaceutical. Also in the embodiment of FIG. 11, the cover 91 is made of a second material whose strength is usually not important (as it has no attachment function) and is usually relatively quick to resorb. Preferably, the cover carries a high or relatively low concentration of the pharmaceutical.

In other embodiments of the present invention, the shank of the cap is coated with a degradation resistant coating in order to retard degradation of the shank and thereby prolong release of the pharmaceutical from within the shank. This is desirable because the shank has an attachment function and so its degradation may lead to an undesirable loosening of the drug-eluting component.

Figure 12:
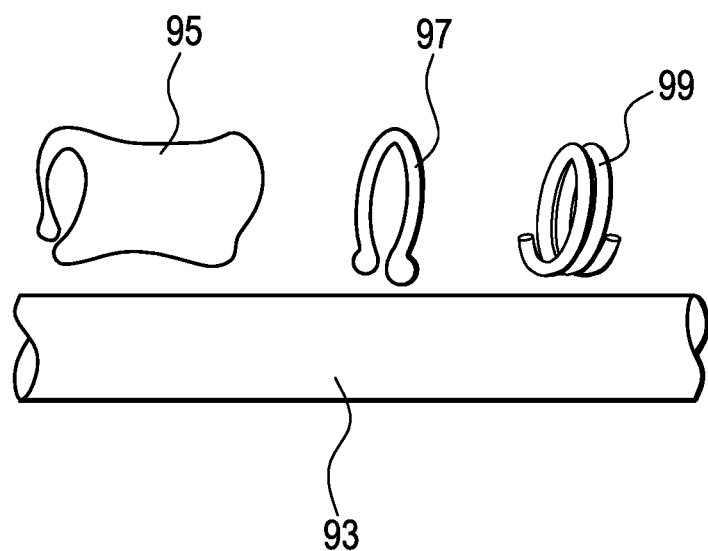
FIG. 12 discloses a split cover, a split ring and a coil for covering a rod.

Now referring to FIG. 12, there is provided a spinal rod cover comprising a pharmaceutical compound, wherein the cover comprises:
 a) a split-annulus defining a longitudinal axis.

In some embodiments of the present invention, the device covers a spinal rod implant 93, and is preferably in the form of a split-annulus 95, a split-ring 97 or a coil 99. Preferably, the diameter of such a device nearly coincides with that of the spinal rod implant, and is preferably slightly smaller than that of the spinal rod implant, so as to provide a snap fit thereon. Flanges or tynes may also be provided on the device in order to prevent device detachment. These features are manufactured from slower degrading materials having a mechanical function. They may attach by wrap-around or interference attachment and be made of delayed degradation biomaterials. Alternatively, the base device can be modified for better cap attachment.

There are several benefits to using the rod cover device of the present invention. First, it possesses a relatively simple geometry. Second, as most rods used in spinal surgery are simple cylinders, a single rod cover device of the present invention can accommodate the rods of several different manufacturers. Third, the rod cover offers ease of placement because the rod always presents an orientation that lends to placing a cover, unlike a screw cap that requires a unidirectional approach. In addition, because spinal rods extend virtually over the entire footprint of the conventional spinal implant system, it is possible to cover a large percentage of the system's footprint by using rod cover devices.

The dose of pharmaceutical delivered by the rod cover as well as its duration can be increased by increasing the thickness, length, or surface area of the rod cover.

Use of the rod cover device further allows the surgeon to concentrate the pharmaceutical along the length of the rod, rather than at specific points along the rod (such as the pedicle screw location). For example, if the surgeon desires to protect a small area, the surgeon can use a split-ring embodiment of the rod cover device. If the surgeon desires to protect a large area, the surgeon can use a split-annulus or coil embodiment of the rod cover device. In some embodiments, the rod cover device can be manufactured by an inexpensive extrusion manufacturing process, thereby lowering manufacturing costs.

Figure 13:
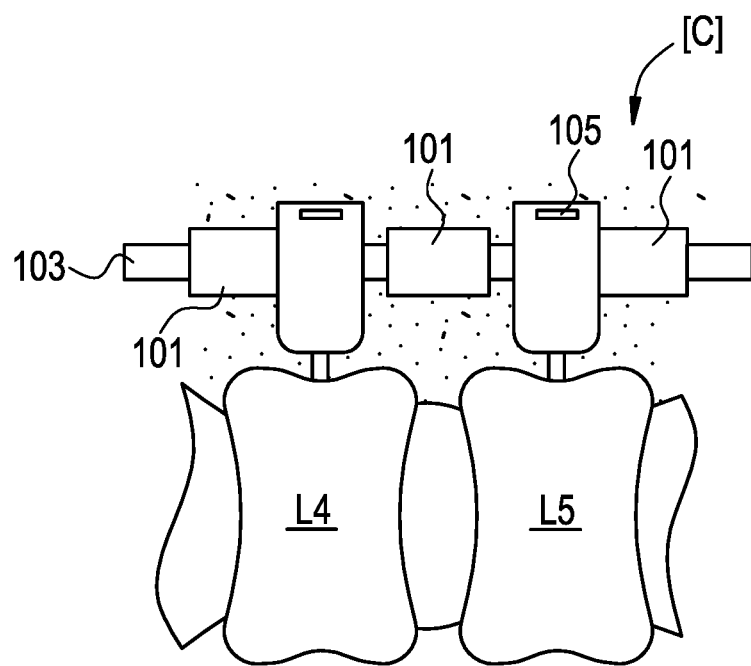
FIG. 13 discloses a drug concentration around a spinal assembly having a rod cover of the present invention.

Now referring to FIG. 13, there is provided a side view of a rod cover device 101 of the present invention attached to a spinal implant system that is implanted in a spine, wherein the system comprises rods 103 and screws 105. This FIG. 13 can be contrasted with FIG. 4 in order to appreciate the difference in concentration profiles afforded by the cap versus the rod cover. Whereas the screw cap provides a high concentration [C] of the pharmaceutical present only in the regions adjacent the screw, the rod cover provides high concentration virtually everywhere along the length of the implant system. Moreover, it is noted that the complex interior polyaxial surfaces of the pedicle screw are located very adjacent the ends of the rod cover devices. Therefore, it is believed that these complex interior polyaxial surfaces of the pedicle screw will likely be bathed in the pharmaceutical provided by the ends of the rod cover devices. It appears that only the area around the screw heads are far from the rod covers and so will have a relatively lower concentration of the pharmaceutical.

Figure 14A:
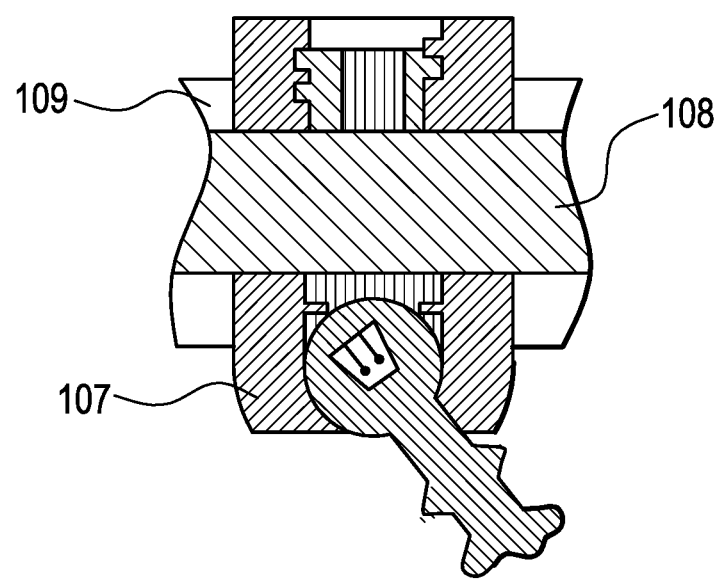
FIG. 14a discloses a cross section of a spinal assembly comprising a polyaxial bone screw, a rod and a rod cover.

FIG. 14a provides a typical cross-section of an assembled polyaxial pedicle screw 107 and rod 108 covered by a split annulus embodiment 109. It is observed that the screw has many complex interfaces that are within its interior and so are shielded from the patient's circulatory and immune systems. Without wishing to be tied to a theory, it is believed that these shielded areas are the locations most susceptible to delayed and chronic infections. Bathing these surfaces in anti-microbial pharmaceutical may prevent these infections.

Figure 14B:
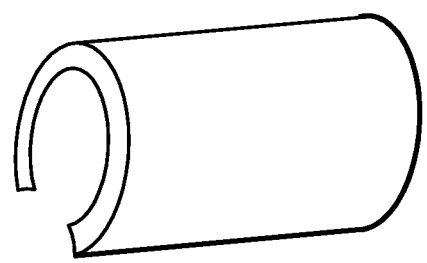
FIG. 14b disclose a spinal rod cover.
Figure 14C:
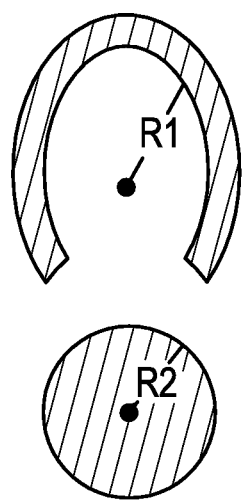
FIG. 14c discloses cross sections of a spinal rod cover and rod.

Now referring to FIGS. 14*b-c*, preferably, the rod cover device of the present invention has a split annulus design. The split annulus 111 preferably features a radius R1 that is just slightly smaller than the radius R2 of the corresponding rod 113, so that the rod covered can be snapped on and secured. Preferably, the rod cover describes an arc of between about 200 degrees and about 300 degrees. If the angle is less than 200 degrees, the rod cover may not attach securely to the rod. If the angle is greater than 300 degrees, there may be difficulty in providing an opening large enough to allow the rod cover to envelope the rod.

The material of construction for the rod cover typically is a homogenous composition, and is preferably amenable to extrusion processing. When the rod cover is made by an extrusion process, the extruded piece may additionally be cut to length intra-operatively by the surgeon in order to obtain the appropriately sized device. It is believed that the extruded rod cover would represent one of the least costly methods of making the rod cover device of the present invention.

In some embodiments, the rod cover device is a segmented annulus having a plurality of slits. Now referring to FIG. 15*a-b*, there is provided a spinal rod cover 121 comprising a pharmaceutical compound, wherein the cover comprises:
a) an annular base 123 defining a longitudinal axis and comprising:
  i) a plurality of slits 125 extending substantially perpendicular to the longitudinal axis,
  ii) a plurality of depressions 127 between the slits.

The plurality of slits allow the surgeon who has determined the appropriate length of the rod cover to snap off the appropriate length of the rod cover at one of the plurality of fracture points beneath the slits. This provides the surgeon with an ability to select an incremental rod cover length that corresponds with the length of rod existing between adjacent pedicle screws.

Figure 15A:
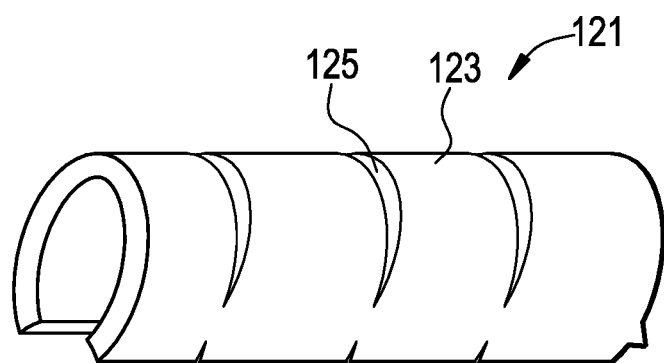
FIG. 15a discloses a spinal rod cover having slits.
Figure 15B:
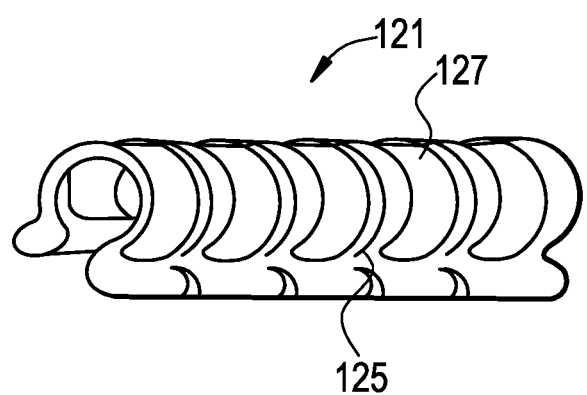
FIG. 15b discloses a spinal rod cover having slits and depressions.
Figure 16A:
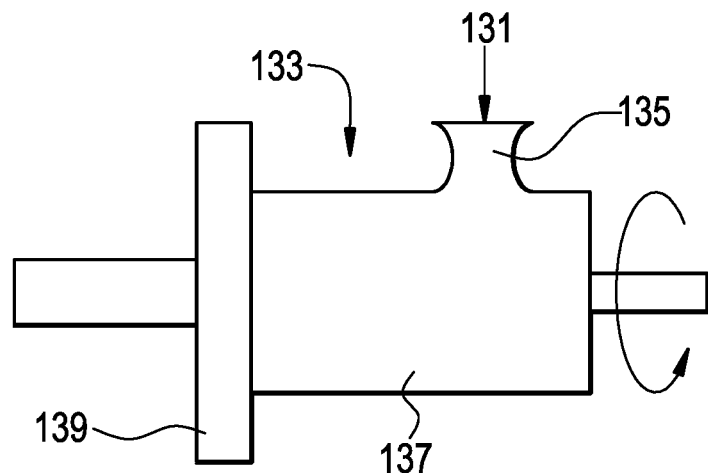
FIGS. 16a and 16b disclose a machine for making spinal rod covers.
Figure 16B:
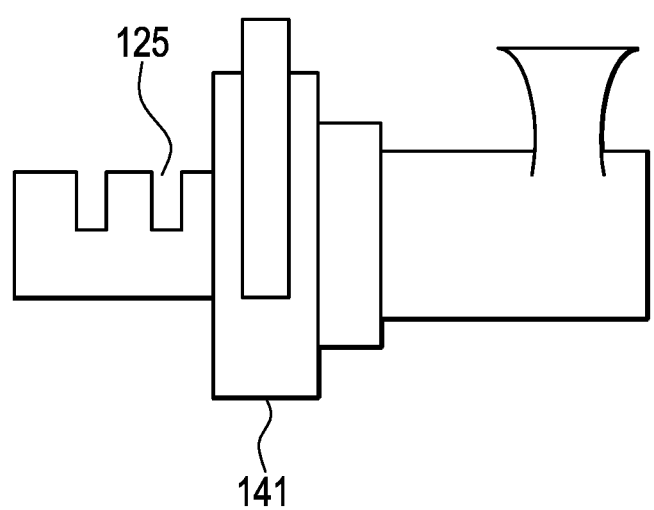

Of note, the segmented rod cover of FIGS. 15*a-b* may also be made via an extrusion process. As shown in FIGS. 16*a-b*, the material to be extruded 131 enters the extruder 133 via its funnel 135, is sent forward by the extruder's ram 137 into a die 139 wherein it takes its extruded form. Prior to exiting the extruder, the extruded part is fed into a chopper 141 that forms the plurality of slits at the desired spacing.

Figure 17:
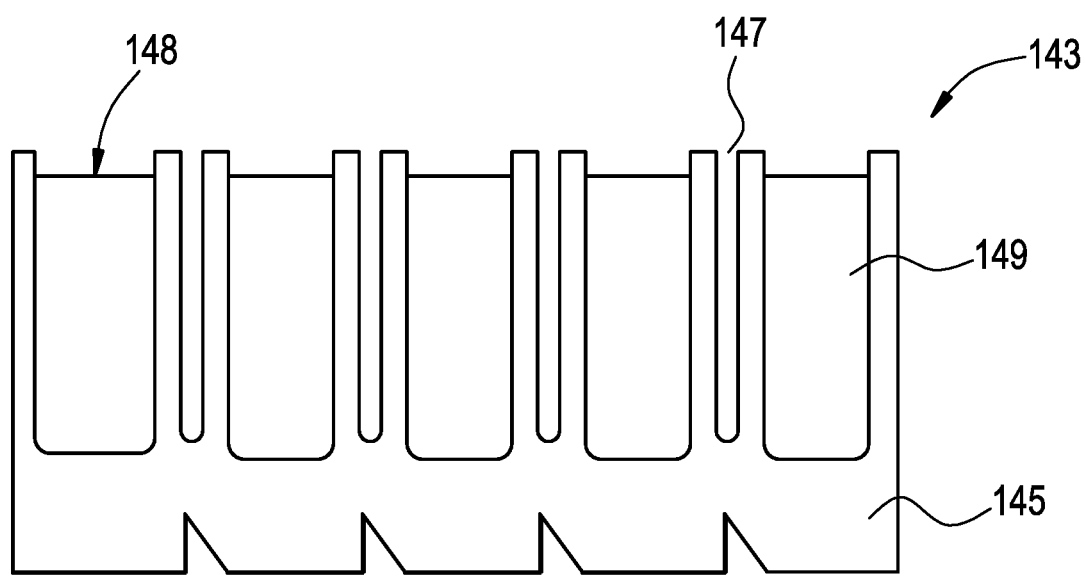
FIG. 17 discloses a spinal rod cover having slits and depressions.

In some embodiments, the rod cover device comprises two components. Now referring to FIG. 17, there is provided a spinal rod cover 143 comprising a pharmaceutical compound, wherein the cover comprises:
a) a split annulus 145 defining a longitudinal axis and comprising:
  i) a plurality of slits 147 extending substantially perpendicular to the longitudinal axis,
  ii) a plurality of depressions 148 between the slits, and
b) a carrier material 149 associated with each depression, wherein the carrier material carries the pharmaceutical compound.

The split annulus has first and second faces each other and first and second ends. The snap-on annulus of the rod cover device is preferably rigid and slow-resorbing. Its main function is to provide a means for attaching to the rod. The function of the carrier material is to deliver the pharmaceutical to the tissue of interest.

Figure 18:
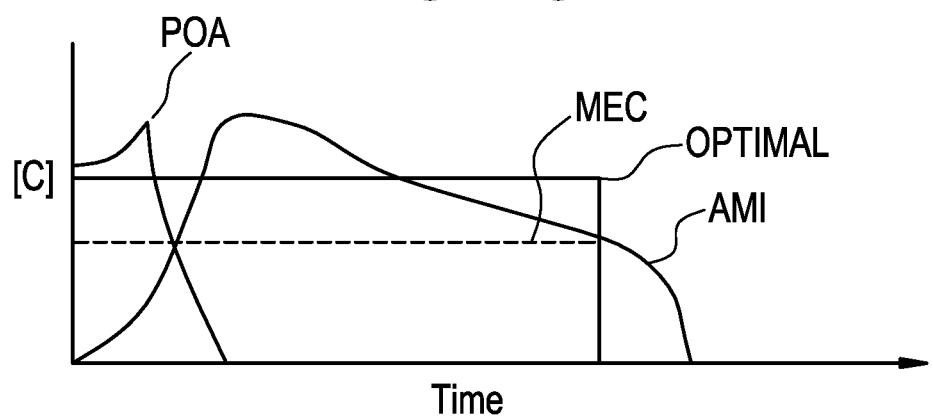
FIGS. 18-20 shows graphs of the concentration profiles of various drug delivery approaches over time.

Now referring to FIG. 18, there is provided a graph of the change in concentration of a drug at a given location as a function of time for a variety of drug administration regimens. "MEC" refers to the "minimum effective concentration" of a drug required to attain a given therapeutic effect. "AMI" refers to the "Anti-Microbial Implant" of the present invention. "POA" refers to a prophylactic oral antibiotic administration. "OPTIMAL" refers to the optimal drug elution profile.

The optimal drug elution profile is linear and terminates abruptly with the drug concentration always remaining above the MEC. In general, prophylactic oral antibiotics (POA) spike early and then dissipate within about a week of their administration. Typically, the implanted device volume and surface area are large compared to these variables over time. An implanted device that erodes or degrades over time typically diminishes in both size and surface area over time—thus, if elution depends on implant volume or surface area, drug dose is dependent on these time-based geometric changes. This is especially true for surface-eroding delivery systems. Thus, the drug elution profile of the AMI of the present invention will likely experience a "mini-spike" and then diminish over time. The tail-end of the drug elution profile of a surface-eroding AMI of the present invention will taper more aggressively as its surface area is reduced.

Figure 19:
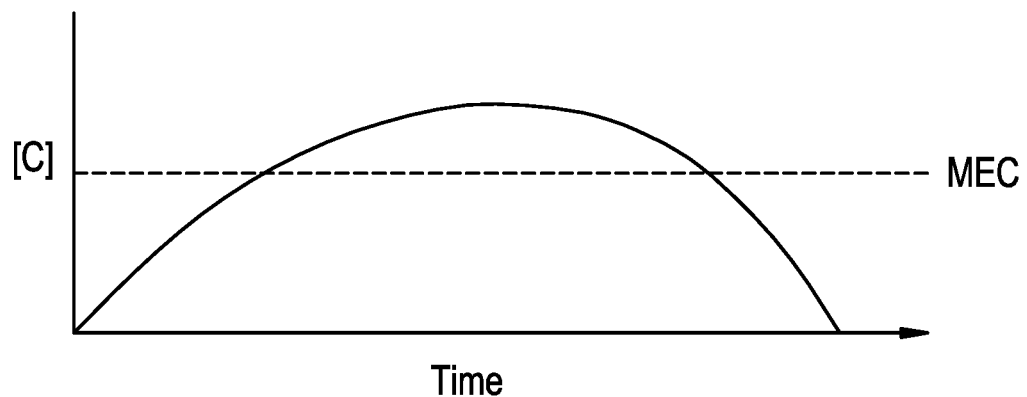

Now referring to FIG. 19, there is provided a depiction of the concentration profile over time of a drug eluting from a hydrolysable drug delivery system. One such hydrolysable drug delivery system is PLLA. In such a system, it is expected that volume, drug diffusability from within the implant, surface area and erodability would be important. These systems typically have a more gradual elution profile with few linear regions. Bulk material loss and surface changes are combined with diffusion from the implanted PLLA delivery vehicle, so three variables all impact the elution profile to make it non-linear and thus less predictable.

Figure 20:
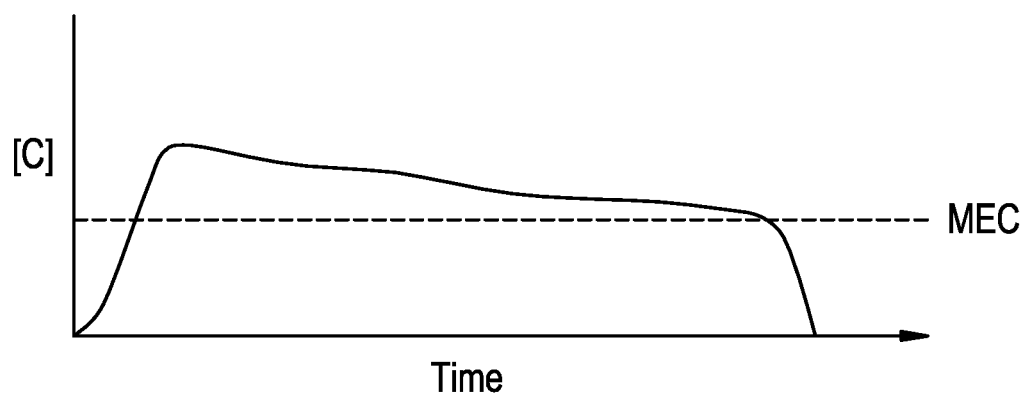

Now referring to FIG. 20, there is provided a concentration profile over time of a drug eluting from a surface-eroding drug delivery system. Exemplary surface eroding hydrolysable drug delivery systems include polysaccharides and linear anhydrides. In such a system, it is expected that volume, drug concentration and surface area would be important. These systems typically produce an initial concentration spike followed by a gradual diminishing ramp profile.

In some embodiments, the device is placed into bony voids created by surgery in order to eliminate or reduce the formation of a post-surgical hematoma—the bacterial petri dish that enables many post-operative infections.

Figure 21A:
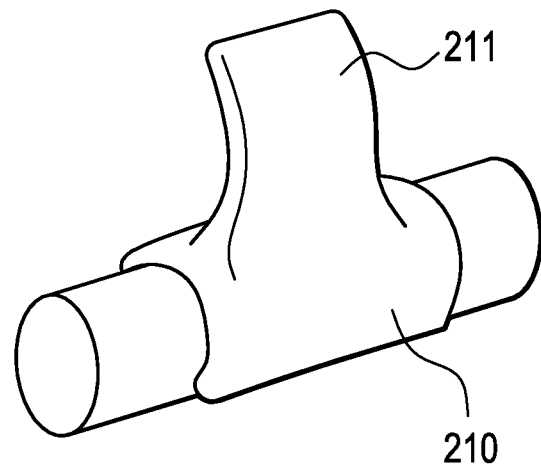
FIGS. 21a-21e represent embodiments of the rod cover having extensions.
Figure 21B:
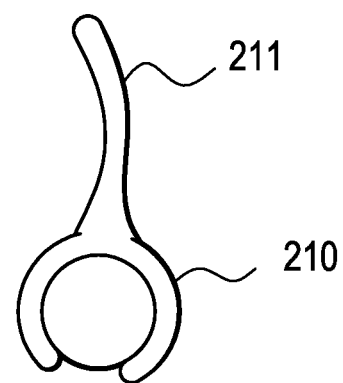
Figure 21C:
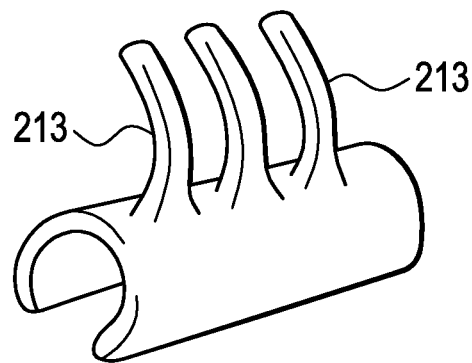
Figure 21D:
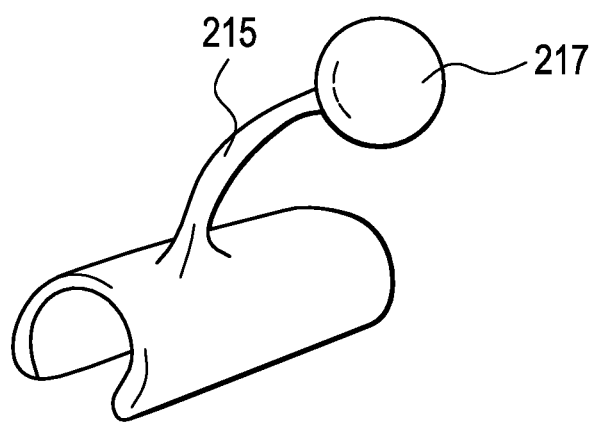
Figure 21E:
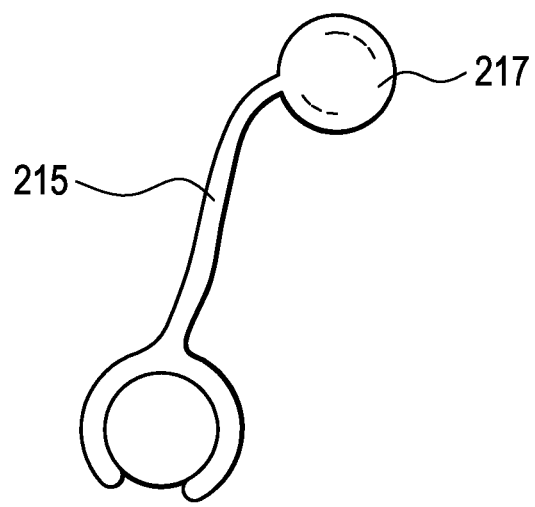

Now referring to FIGS. 21*a-21e*, there are provided rod covers of the present invention having extensions. FIGS. 21*a-b* show a single wide extension 211 extending from the annulus 210 for the length of the rod cover. FIG. 21*c* shows a plurality of extensions 213 extending from the annulus. FIG. 21*c* shows an extension 215 terminating in a head 217 extending from the annulus.

Extensions of material from the rod cover are contemplated. These material extensions are contemplated to have mechanical or drug-eluting functions. Since the rod cover interfaces directly with the rod or the sides of the screw head in direct contact with the rod, a rod cover material extension could be placed proximal to a screw head (surrounding it or placed superficially) for either mechanical or drug-eluting purposes. Placement of a drug eluting extension proximally to the screw head would approximate complete coverage of the entire rod-screw construct with the locally eluted drug. Additionally, rod cover material extensions could interface with local tissues either mechanically or pharmaceutically. A strut of material extending from the rod cover could be used to prevent soft tissue encroachment on a healing wound site. Similarly, a strut of material extending from the rod cover could be used to locate a drug-eluting depot distally from the rod and rod cover. Distal placement of the drug eluting depot would enable greater local penetration/concentration of the eluted pharmaceutical agent. Finally, the material extension could be embodied as a sheet, flag, or tether that is attached at some point to the rod cover material. In this case, the material extension could be an entirely separate material system with a different function, such as a hemostat, an anti-adhesion barrier, a drug depot (pain medication or anti-bacterial compounds), etc. The purpose of attaching a separate device as an extension to the rod cover is to co-locate this new material or second device with the rod cover, thereby decreasing the propensity for migration of the materials away from the rod.

Figure 22A:
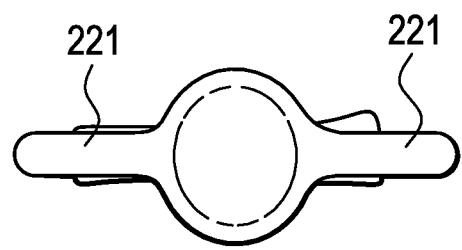
FIGS. 22a-22e represent embodiments of the screw cap having extensions.
Figure 22B:
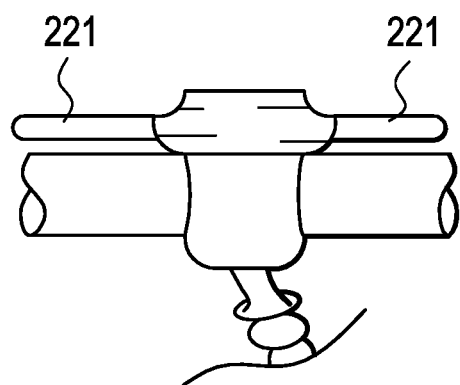
Figure 22C:
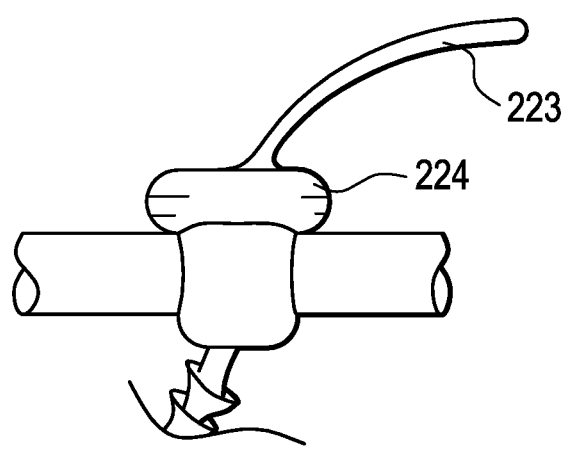
Figure 22D:
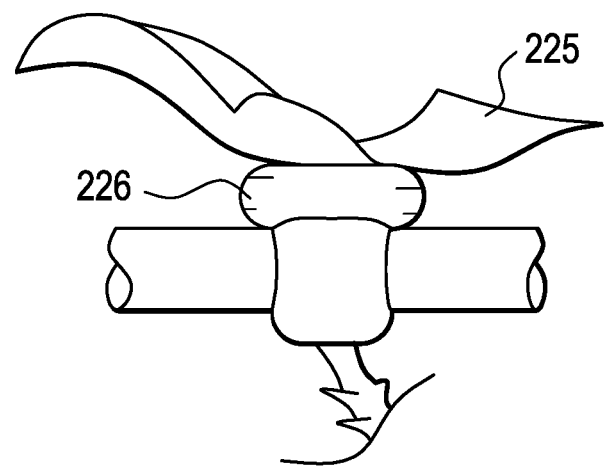
Figure 22E:
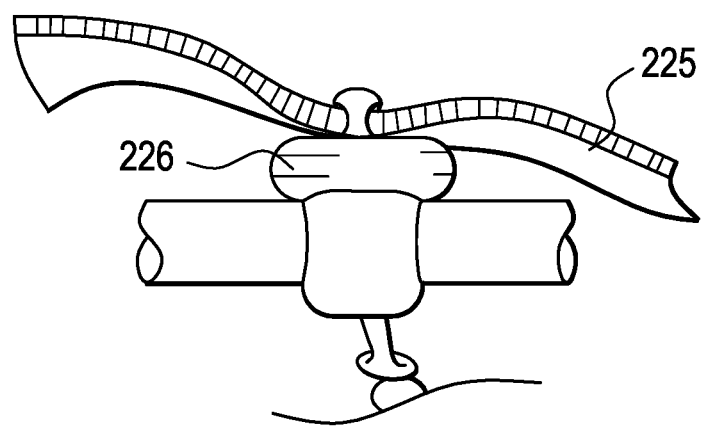

Now referring to FIGS. 22a-22e, there are provided screw caps of the present invention having extensions. FIGS. 22a-b show a plurality of extension 221 extending laterally from the screw cap 222. FIG. 22c shows an extension 223 axially extending from the screw cap 224. FIGS. 22d-e shows a fabric extension 225 attached to the screw cap 226.

Material extensions from the screw cap are also contemplated in this invention. The purpose of these extensions can be to provide cap-to-cap screw head connections, cap-to-rod connections, or combinations of device interconnections. Additionally, the material extensions from the screw cap can have mechanical functions with surrounding tissues. For example, a strut of screw cap material could be used to prevent surrounding soft tissues from touching one another or to prevent local soft tissue encroachment on a wound space. Alternatively, the screw cap extension could be used to deploy an eluting drug agent into the surrounding tissues distal to the screw location. With a material extension, screw cap drug-eluting materials are placed distally from the screw cap and enable increased distribution and diffusion of the drugs. Additionally, a large bolus of material can be tethered to the screw cap extension thereby placing a significant portion of drug eluting material distal to the screw cap location, but locally tethered to the screw cap. Finally, the screw cap material extension could be embodied as a sheet or flag of material, perhaps different from the screw cap material. In one embodiment, such a material could be a woven textile of hemostat that is attached to the screw cap. The purpose of such an embodiment would be to positively co-locate a sheet of material with the screw cap, thereby decreasing this material's propensity to migrate in the wound after implantation.

The rod cover and screw cap of the present invention may be made from biocompatible materials that are either resorbable or non-resorbable.

In some embodiments, the rod cover and screw cap are non-resorbable. These non-resorbable devices also prevent bacterial colonization from occurring.

Preferred bioresorbable materials which can be used to make components of the present invention include bioresorbable polymers or copolymers, preferably selected from the group consisting of hydroxy acids, (particularly lactic acids and glycolic acids; caprolactone; hydroxybutyrate; dioxanone; orthoesters; orthocarbonates; and aminocarbonates. Preferred bioresorbable materials also include natural materials such as chitosan, collagen, cellulose, fibrin, hyaluronic acid; fibronectin, and mixtures thereof. However, synthetic bioresorbable materials are preferred because they can be manufactured under process specifications which insure repeatable properties.

A variety of bioabsorbable polymers can be used to make the device of the present invention. Examples of suitable biocompatible, bioabsorbable polymers include but are not limited to polymers selected from the group consisting of aliphatic polyesters, poly(amino acids), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, biomolecules (i.e., biopolymers such as collagen, elastin, bioabsorbable starches, etc.) and blends thereof. For the purpose of this invention aliphatic polyesters include, but are not limited to, homopolymers and copolymers of lactide (which includes lactic acid, D-, L- and meso lactide), glycolide (including glycolic acid), ε-caprolactone, p-dioxanone (1,4-dioxan-2-one), trimethylene carbonate (1,3-dioxan-2-one), alkyl derivatives of trimethylene carbonate, δ-valerolactone, β-butyrolactone, χ-butyrolactone, ε-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan-2-one, 2,5-diketomorpholine, pivalolactone, χ,χ-diethylpropiolactone, ethylene carbonate, ethylene oxalate, 3-methyl-1,4-dioxane-2,5-dione, 3,3-diethyl-1,4-dioxan-2,5-dione, 6,8-dioxabicycloctane-7-one and polymer blends thereof. Poly(iminocarbonates), for the purpose of this invention, are understood to include those polymers as described by Kemnitzer and Kohn, in the *Handbook of Biodegradable Polymers*, edited by Domb, et. al., Hardwood Academic Press, pp. 251-272 (1997). Copoly(ether-esters), for the purpose of this invention, are understood to include those copolyester-ethers as described in the Journal of Biomaterials Research, Vol. 22, pages 993-1009, 1988 by Cohn and Younes, and in Polymer Preprints (ACS Division of Polymer Chemistry), Vol. 30(1), page 498, 1989 by Cohn (e.g. PEO/PLA). Polyalkylene oxalates, for the purpose of this invention, include those described in U.S. Pat. Nos. 4,208,511; 4,141,087; 4,130,639; 4,140,678; 4,105,034; and 4,205,399. Polyphosphazenes, co-, ter- and higher order mixed monomer-based polymers made from L-lactide, D,L-lactide, lactic acid, glycolide, glycolic acid, para-dioxanone, trimethylene carbonate and ε-caprolactone such as are described by Allcock in *The Encyclopedia of Polymer Science*, Vol. 13, pages 31-41, Wiley Intersciences, John Wiley & Sons, 1988 and by Vandorpe, et al in the *Handbook of Biodegradable Polymers*, edited by Domb, et al, Hardwood Academic Press, pp. 161-182 (1997). Polyanhydrides include those derived from diacids of the form HOOC—$C_6H_4$—O—$(CH_2)_m$—O—$C_6H_4$—COOH, where m is an integer in the range of from 2 to 8, and copolymers thereof with aliphatic alpha-omega diacids of up to 12 carbons. Polyoxaesters, polyoxaamides and polyoxaesters containing amines and/or amido groups are described in one or more of the following U.S. Pat. Nos. 5,464,929; 5,595,751; 5,597,579; 5,607,687; 5,618,552; 5,620,698; 5,645,850; 5,648,088; 5,698,213; 5,700,583; and 5,859,150. Polyorthoesters such as those described by Heller in *Handbook of Biodegradable Polymers*, edited by Domb, et al, Hardwood Academic Press, pp. 99-118 (1997).

Preferably, the bioresorbable material is selected from the group consisting of poly(lactic acid) ("PLA") and poly(glycolic acid)("PGA"), and copolymers thereof. These materials are preferred because they possess suitable strength and biocompatibility, display desirable resorption profiles, and have a long history of safe in vivo use. In general, PLA is a desirable because it typically has a resorption time exceeding 12 months, whereas PGA resorbs fairly quickly (having a resorption time of less than 12 months). However, PLA can require many years to completely resorb, and so is more likely to produce foreign-body reactions. Therefore, more preferably, the material is a PLA/PGA copolymer, more preferably the copolymer comprises between 80 wt % and 99 wt % lactic acid (as PLA), and between 1 wt % and 20 wt % glycolic acid (as PGA). Copolymers within these ranges provide the proper balance between the strength and the resorption time of the ligament.

The term "pharmaceutical" or "drug", as used herein, refers to any substance used internally as a medicine for the treatment, cure, or prevention of a disease or disorder, and includes but is not limited to immunosuppressants, antioxidants, anesthetics, analgesics, chemotherapeutic agents, steroids (including retinoids), hormones, antibiotics or antimicrobials, antivirals, antifungals, antiproliferatives, antihistamines, anticoagulants, antiphotoaging agents, melanotropic peptides, nonsteroidal and steroidal anti-inflammatory compounds, antipsychotics, and radiation absorbers, including UV-absorbers.

Non-limiting examples of pharmacological materials include anti-infectives such as nitrofurazone, sodium propionate, antibiotics, including penicillin, tetracycline, oxytetracycline, chlorotetracycline, bacitracin, nystatin, streptomycin, neomycin, polymyxin, gramicidin, chloramphenicol, erythromycin, and azithromycin; sulfonamides, including sulfacetamide, sulfamethizole, sulfamethazine, sulfadiazine, sulfamerazine, and sulfisoxazole, and anti-virals including idoxuridine; antiallergenics such as antazoline, methapyritene, chlorpheniramine, pyrilamine prophenpyridamine, hydrocortisone, cortisone, hydrocortisone acetate, dexamethasone, dexamethasone 21-phosphate, fluocinolone, triamcinolone, medrysone, prednisolone, prednisolone 21-sodium succinate, and prednisolone acetate; desensitizing agents such as ragweed pollen antigens, hay fever pollen antigens, dust antigen and milk antigen; vaccines such as smallpox, yellow fever, distemper, hog cholera, chicken pox, antivenom, scarlet fever, diphtheria toxoid, tetanus toxoid, pigeon pox, whooping cough, influenzae rabies, mumps, measles, poliomyelitic, and Newcastle disease; decongestants such as phenylephrine, naphazoline, and tetrahydrazoline; miotics and anticholinesterases such as pilocarpine, esperine salicylate, carbachol, diisopropyl fluorophosphate, phospholine iodide, and demecarium bromide; parasympatholytics such as atropine sulfate, cyclopentolate, homatropine, scopolamine, tropicamide, eucatropine, and hydroxyamphetamine; sympathomimetics such as epinephrine; sedatives and hypnotics such as pentobarbital sodium, phenobarbital, secobarbital sodium, codeine, (a-bromoisovaleryl) urea, carbromal; psychic energizers such as 3-(2-aminopropyl) indole acetate and 3-(2-aminobutyl) indole acetate; tranquilizers such as reserpine, chlorpromayline, and thiopropazate; anesthetics, such as novicaine and bupivacaine; androgenic steroids such as methyl-testosterone and fluorymesterone; estrogens such as estrone, 17-flestradiol, ethinyl estradiol, and diethyl stilbestrol; progestational agents such as progesterone, megestrol, melengestrol, chlormadinone, ethisterone, norethynodrel, 19-norprogesterone, norethindrone, medroxyprogesterone and 17-0-hydroxyprogesterone; humoral agents such as the Prostaglandins, for example PGEI, PGE2 and PGF2; antipyretics such as aspirin, sodium salicylate, and salicylamide; antispasmodics such as atropine, methantheline, papaverine, and methscopolamine bromide; antimalarials such as the 4-aminoquinolines, 8-aminoquinolines, chloroquine, and pyrimethamine, antihistamines such as diphenhydramine, dimenhydrinate, tripelennamine, perphenazine, and chlorphenazine; cardioactive agents such as dibenzhydroflume thiazide, flumethiazide, chlorothiazide, and aminotrate; nutritional agents such as vitamins, natural and synthetic bioactive peptides and proteins, including growth factors, cell adhesion factors, cytokines, and biological response modifiers.

The active compound is included in the composition in an amount sufficient to deliver to the host patient an effective amount to achieve a desired effect. The amount of drug or biologically active agent incorporated into the composition depends upon the desired release profile, the concentration of drug required for a biological effect, and the desired period of release of the drug.

The concentration of active compound in the composition will also depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The composition may be administered in one dosage, or may be divided into a number of smaller doses to be administered at varying intervals of time.

The biologically active substance is typically present in the composition in the range from about 0.1 percent to about 20 percent by weight, more particularly from about 0.5 percent to about 20 percent by weight relative to the total weight of the composition, and more typically, between approximately 1 percent to about 15 percent by weight, and more. Another preferred range is from about 2 percent to about 10 percent by weight. For very active agents, such as growth factors, preferred ranges are less than 1% by weight, and less than 0.0001%.

REFERENCES

1. J Bone Joint Surg (Br), 63:342-53, 1981
2. J Bone Joint Surg (Br), 87(2): 249-56, 2005
3. J. Neurosurg., 69: 687-91, 1988
4. J. Neurosurg.,73:383-386, 1990
5. J Neurosurg.60:724-726, 1984.
6. Spine 30(12):1460-5, 2005.
7. Spine 28(13):1475-80, 2003.
8. Spine 24(18):1909-12, 1999.
9. Spine 26(18):1990-6, 2001.
10. J Bone Joint Surg [Am] 77:524-9, 1995.
11. J Neurosurg 69:687-91, 1988.
12. N Engl J Med 350(14):1422-1429, 2004.
13. 2003 communication from Johns Hopkins spine surgeon, Dr. Sponseller.

We claim:

1. A spinal rod cover comprising a pharmaceutical compound, wherein the cover comprises an annular base defining a longitudinal axis and comprising:
   i) a plurality of slits extending substantially perpendicular to the longitudinal axis, and
   ii) a plurality of fracture points beneath the slits.

2. The cover of claim 1 further comprising a carrier material associated with each slit.

3. The cover of claim 2 wherein the carrier material carries the pharmaceutical compound.

4. The cover of claim 3 wherein the pharmaceutical compound is an anti-microbial compound.

5. The cover of claim 1 further comprising an extension.

6. The cover of claim 1 further comprising a plurality of depressions between the slits.

\* \* \* \* \*